United States Patent [19]

Narayanan et al.

[11] Patent Number: 5,476,662
[45] Date of Patent: Dec. 19, 1995

[54] PESTICIDE OR HERBICIDE POLYMER COMPLEXES FOR FORMING AQUEOUS DISPERSIONS

[75] Inventors: Kolazi S. Narayanan, Palisades Park; Ratan K. Chaudhuri, Butler, both of N.J.

[73] Assignee: ISP Investments Inc., Wilmington, Del.

[21] Appl. No.: 975,812

[22] Filed: Nov. 13, 1992

[51] Int. Cl.$^6$ .................................................. A01N 25/10
[52] U.S. Cl. ...................... 424/409; 424/405; 424/78.33; 424/78.35; 424/78.37
[58] Field of Search ...................... 424/405, 409, 424/489, 78.33, 78.35, 78.37; 71/85, 64.08; 504/116, 142, 143, 149, 308; 514/628

[56] References Cited

U.S. PATENT DOCUMENTS

| | | | |
|---|---|---|---|
| 3,996,347 | 12/1976 | Breslow et al. | 424/78.33 |
| 4,878,941 | 11/1989 | Theodoridis | 71/93 |
| 4,911,952 | 3/1990 | Doane et al. | 427/213.31 |
| 5,169,645 | 12/1992 | Shukla et al. | 424/499 |

OTHER PUBLICATIONS

Gantrez S-95 ISP Technologies Inc. M.S.O.S. #349 B Rev. Jul. 1990.

*Primary Examiner*—Thurman K. Page
*Assistant Examiner*—N. Levy
*Attorney, Agent, or Firm*—Jules E. Goldberg; William J. Sapone; Joshua J. Ward

[57] ABSTRACT

Various liquid or low melting pesticide and herbicide formulations, previously formulated with organic solvents, are combined with a polymer in solution and co-precipitated to form a polymer complex which captures the pesticide or herbicide yet exists as a solid at ambient conditions. By preparing the pesticide or herbicide formulation as a solid complex, storage and handling of the formulation is possible without the potential for organic solvent emission. When the solid polymer complex is placed in water, a stable aqueous dispersion of the pesticide or herbicide is achieved as the polymer inhibits flocculation, with approximately 100% recovery of the pesticide or herbicide.

3 Claims, 2 Drawing Sheets

PESTICIDE OR HERBICIDE POLYMER COMPLEXES FOR FORMING AQUEOUS DISPERSIONS

TECHNICAL FIELD

This invention relates to pesticides and herbicides which form complexes with a polymer for storage and handling as a solid, the pesticides and herbicides instantly dispersable into a stable emulsion when added to water.

BACKGROUND OF THE INVENTION

Various pesticides and herbicides are available in liquid form such as various members of the chloroacetanilide family including metolachlor, acetochlor, pretilachlor, dimethachlor, alachlor and butachlor, which exist as oily liquids or low melting solids at ambient conditions. Such materials are usually formulated and applied in combination with various organic solvents.

With increased attention to lowering solvent emissions and to ease handling requirements, it is preferred to use pesticides and herbicides which may be handled in solid form for storage and transport. It is also desirable to provide a solid pesticide or herbicide which may be dissolved, rather than in an organic solvent, in water at the time of application. To be successful, the material must form a uniform dispersion to assure even application and maintain a stable emulsion for a time sufficient to complete the application. However, many pesticides and herbicides such as members of the chloroacetanilide family, are not considered suitable for use in a solid form, nor for preparation as aqueous emulsions.

SUMMARY OF THE INVENTION

It is an object of the present invention to provide a polymer capable of complexing with a pesticide or herbicide to form a solid material for storage and handling.

It is a further object to provide a polymer complex of a pesticide or herbicide which, when added to water, forms an instant dispersion of the pesticide or herbicide into a stable emulsion, with nearly complete recovery of the pesticide or herbicide.

These and other objects of the present invention are achieved by providing a complex of a polymer and a pesticide or herbicide formulation comprising 10 to 90% by weight pesticide or herbicide coprecipitated with the polymer from a solvent. The complex is instantly dispersable into a stable emulsion in water with substantially complete recovery of the pesticide or herbicide. Preferably, the complex is prepared by providing a maleic acid-methylvinylether alternating copolymer, dissolving the copolymer in a solvent, adding a pesticide or herbicide thereto and co-precipitating to form a solid complex of the polymer and pesticide or herbicide. It has been discovered that the precipitated polymer complex is a solid which captures the pesticide or herbicide, with the solid easily handled using standard solids handling techniques. When added to water, the complex forms an instant dispersion of the pesticide or herbicide into a stable emulsion, with approximately 100% recovery, without the addition of other surfactants.

DETAILED DESCRIPTION OF THE INVENTION

Figure 1:
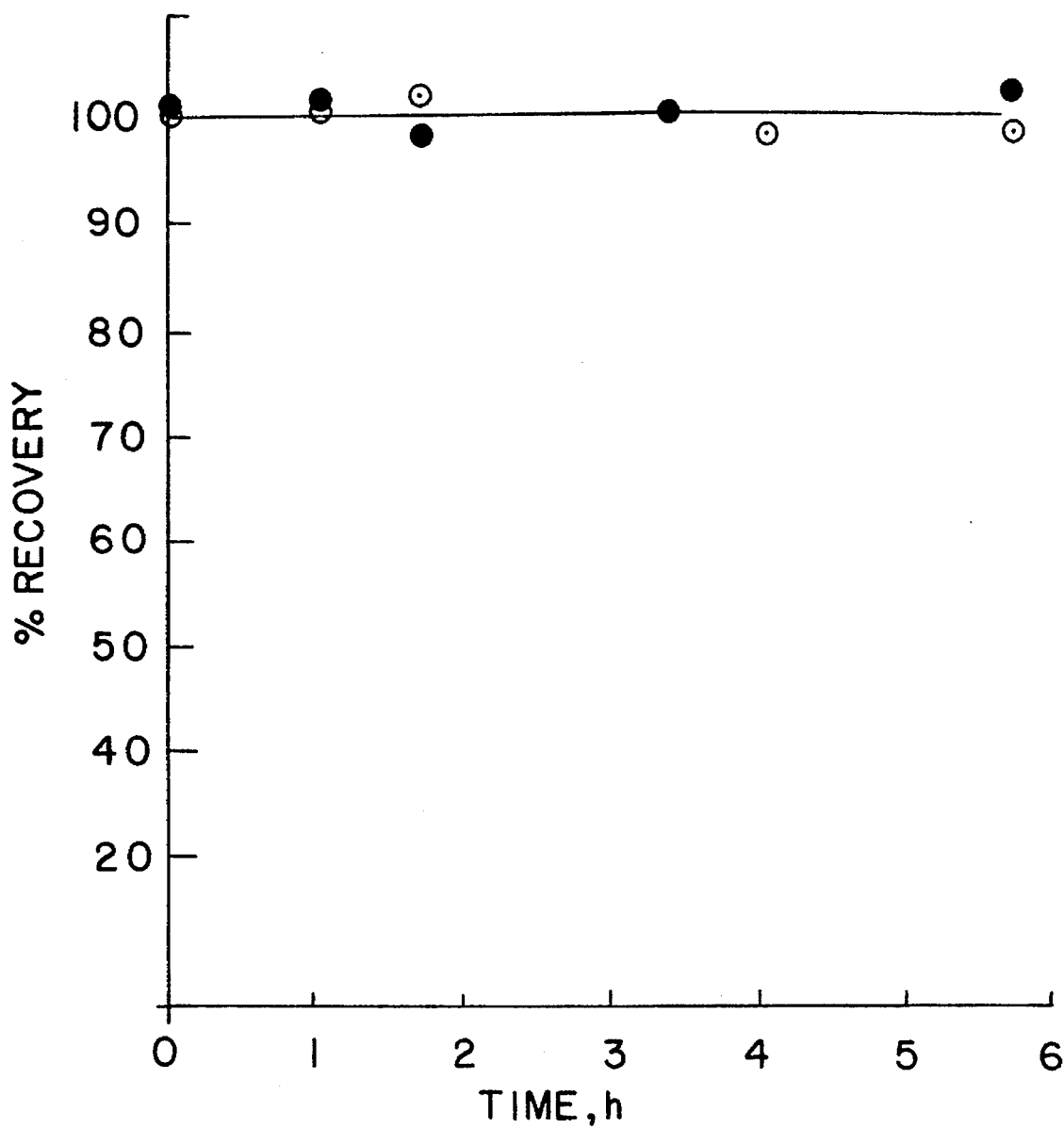
FIG. 1 is a graph showing recovery of an active ingredient after dispersion in a standing sample.

According to the invention, a polymer and a liquid or low melting pesticide or herbicide formulation are combined and co-precipitated from a solvent as a polymer complex. The polymer is preferably a polyacid of the following formula I:

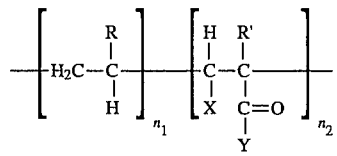

where R is H, $C_1$–$C_{18}$ alkyl, $C_1$–$C_{18}$ alkoxy or aryl;
R' is H or $C_1$–$C_4$ alkyl; X is H, COOH, $COOR_1$ C—N—R
$R_1$, being H or $C_1$–$C_{18}$ alkyl;

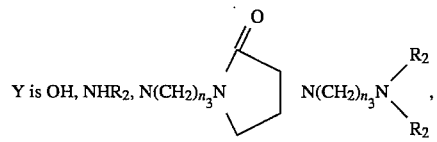

$R_2$ being H or $C_1$–$C_{18}$ alkyl and $n_3$ being 2–4; $n_1$ is 0–10,000; and, $n_2$ is 100–10,000. Preferably, $n_1$ equals $n_2$ equals 500–3000. In one preferred embodiment of the invention, R is $OCH_3$, X is COOH, Y is OH, R' is H, $n_1=n_2=1400$, which is a commercially available polymer known as Gantrez S-95 polymer manufactured by ISP Corporation. However other copolymers may be used.

The pesticide or herbicide should have a molecular geometry such that the molecule can form an insertion complex via hydrogen bonding with the acid groups (C(O)OH) in the polymer matrix. The bond is sufficiently strong to hold the molecule in a bound form to produce a stable emulsion forming conformation after contact with water. In essence, it is believed that electrostatic dispersions are formed where the London-Vander Waals force is overcome by an electrical double layer effect about the particles which prevents flocculation. This is believed to be accomplished by orientation of the hydrophilic part of the bound polymer molecule complex into the water and the hydrophobic part of the polymer molecule complex curved in away from the water. Thus, not only does the solid polymer complex provide a means for storage and handling without organic solvents, but the polymer also promotes stability of the pesticide or herbicide when added to water.

Among the pesticide and herbicide compounds usable in the invention, those preferred are chloroacetanilides having the following formula II:

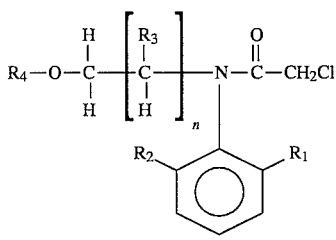

where $R_1$, $R_2$, $R_3$ and $R_4$ are hydrogen or $C_1$–$C_4$ alkyl and n is 0–2. Of course, other pesticides and herbicides having a geometry suitable for forming the polymer complex may be used in the present invention and this invention is not limited to the compounds of Formula II.

In particular, the chloroacetanilides of Table I may be used in the present invention.

TABLE I

|       | Metola chlor | Acetoc hlor | Pretila chlor | Dimetha chlor | Ala chlor | Buta chlor |
|-------|--------------|-------------|---------------|---------------|-----------|------------|
| $R_1$ | Me           | Me          | Me            | Me            | ET        | ET         |
| $R_2$ | ET           | ET          | Me            | Me            | ET        | ET         |
| $R_3$ | Me           | H           | H             | H             | H         | H          |
| $R_4$ | Me           | ET          | Pr            | Me            | Me        | Bu         |
| n     | 1            | 0           | 2             | 2             | 1         | 1          |

The pesticides or herbicides, hereinafter termed active ingredients ("A.I."), to polymer ratio by weight is in the range of 0.1:0.9 to 0.9:0.1, and preferably, the ratios are in the range of 0.3:0.7 to 0.7:0.3, and most preferably, 0.4:0.6 to 0.6:0.4.

The complexes of the invention may be formed by mixing the active ingredient and polymer in a solvent, such as alcohol, heating the mixture for a time sufficient to dissolve the polymer and then evaporating the solvent to precipitate a solid polymer/active ingredient complex, with the AI captured by the polymer. Preferably, the solvent is recovered and reused. Alternatively, the active ingredient is prepared as a suspension, added to an aqueous solution of the polymer, with agitation and possibly addition of an emulsifying agent. A solid complex is obtained by separation, preferably by freeze or spray drying. Such a process avoids organic solvents entirely.

EXAMPLE I 30 grams of metolachlor and 30 grams of Gantrez S-95 polymer were mixed in 200 milliliters of ethanol, to provide a 50–50 ratio active ingredient to polymer. The solution was heated to about 50° C. and agitated for 4–6 hours. The ethanol was then stripped off under reduced pressure, keeping the temperature below 40° C., causing precipitation of a solid, having a weight of about 58 grams. The solid was analyzed by ultraviolet techniques and found to contain 48% metolachlor.

Figure 2:
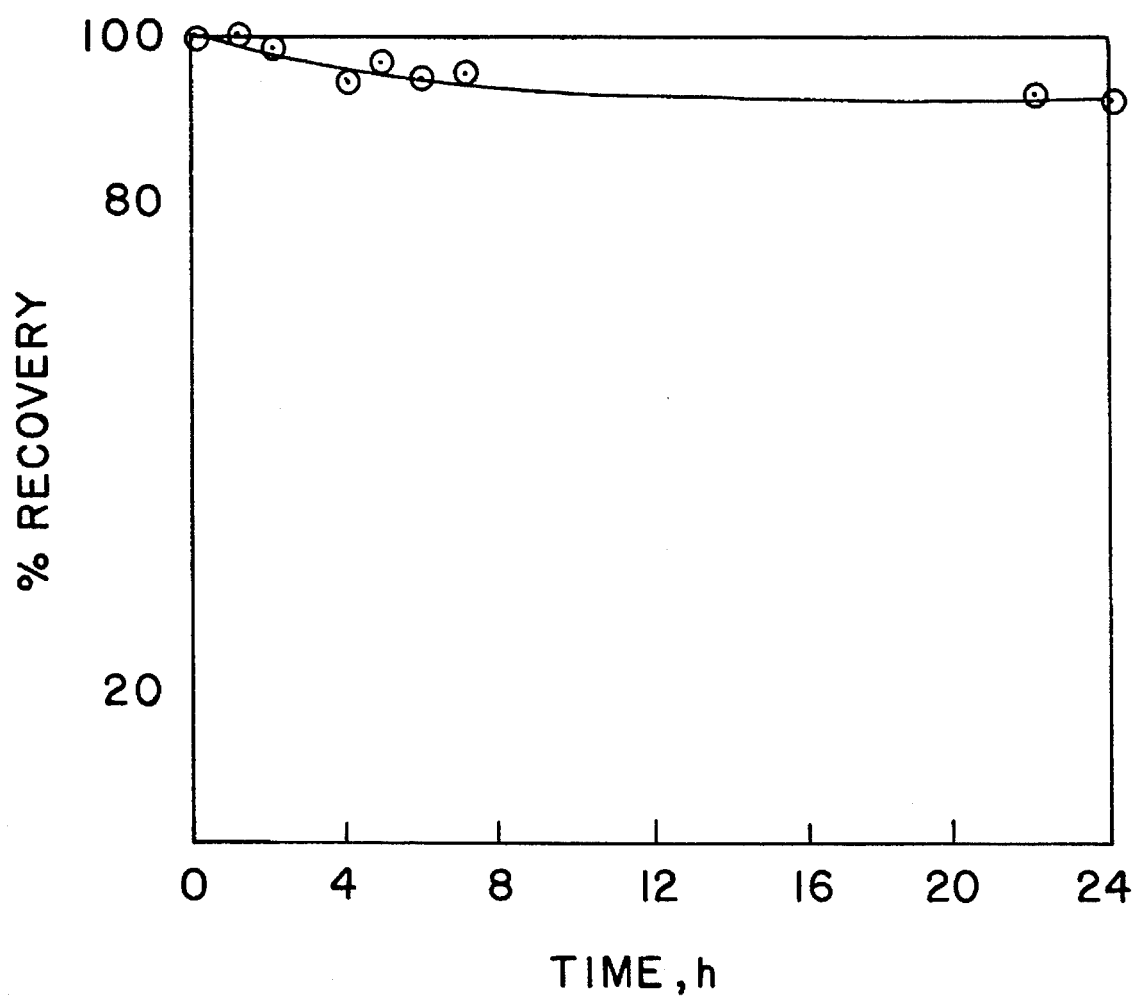
FIG. 2 is a graph showing recovery of an active ingredient after dispersion in a mildly stirred sample.

EXAMPLE II 1 gram of the solid complex of example I was added to 50 milliliters of hard water (342 ppm as $CaCO_3$) to provide a 1% concentration of metolachlor, with the mixture then inverted 20 times. The solid instantly dispersed to form an emulsion. The concentration of metolachlor was monitored by UV absorbance measurements from aliquots diluted in ethanol on both standing samples and on mildly stirred samples, over 24 hours. The percent recovery on the standing samples was 97–100% at 25% and 50% in depth, from the top, showing excellent homogeneity of the dispersion, as shown in FIG. 1. The percent recovery on mildly stirred samples was 90–100% over 24 hours, as shown in FIG. 2.

COMPARATIVE EXAMPLE III 0.5 grams of metolachlor was added to a solution containing 0.5 grams of Gantrez S-95 polymer in water, to form a 1% metolachlor concentration. No coprecipitation step was undertaken. The material was inverted 20 times and no stable emulsion was formed.

EXAMPLE IV

Three samples of metolachlor and Gantrez S-95 polymer were prepared in accordance with example I, except the first contained a 50–50 metolachlor to polymer ratio, the second a 60–40 ratio and the third an 80–20 ratio. In each case, a solid was recovered. Each solid sample was kept at an elevated temperature of 45° C. for four weeks. The results on stability are shown in Table II.

TABLE II

|  | STABILITY | | |
|---|---|---|---|
| SAMPLE | 1 | 2 | 3 |
| RATIO | 50:50 | 60:40 | 80:20 |
| Nature on formation | Solid | Solid | Solid |
| After 4 weeks at 45° C. | Negligible caking but easily disinter able | some caking easily disinter able | honeylike product |
| Dispersibility on formation | Excellent | Excellent | good |
| % Recovery | 100% | — | — |
| Dispersibility after 4 weeks at 45° C. | No change | — | — |

In each case, dispersion on dilution to a 1% concentration was good to excellent, though the 80/20 solid became viscus after four weeks at 45° C.

EXAMPLE V

Example 1 was repeated except 30 grams of maleic acid-butylvinylether copolymer was used in place of the Gantrez S-95 copolymer. A solid complex was formed.

EXAMPLE VI

Example 1 was repeated except 30 grams of polyacrylic acid, commercially obtained from Aldrich, was used in place of the Gantrez S-95. A solid complex was formed.

EXAMPLE VII

Example 1 was repeated except 30 grams of polymethacrylate, commercially obtained from Aldrich, was used in place of the Gantrez S-95 copolymer. A solid complex was formed.

EXAMPLE VIII

Example 1 was repeated except 30 grams of GANTREDONE, a pyro 11 idonylethylmaleamide-methylvinylether-maleic acid copolymer, manufactured by ISP Corporation, was used in place of the Gantrez S-95 copolymer. A solid complex was formed.

EXAMPLE IX

Example 1 was repeated except 45 grams of Gantrez S-95 was used instead of 30 grams. The recovered solid had good thermal stability.

Typically the polymer-AI complex forms an aqueous dispersion without utilizing additional surfactants. However, surfactants and other property modifying agents may be used, depending on the end use application. In addition, to achieve a stable dispersion may require adjustment of the solution pH. This can be accomplished by partially neutralizing the polyacid to form salts. Thus, the polymer AI complex, prior to precipitation, can be adjusted, to produce a solid which will provide an instant aqueous dispersion. The process entails the additional step of adding a neutralizing agent, such as sodium hydroxide or $NaHCO_3$ or $Na_2CO_0$, to the polymer solution to provide a pH greater than 3 and preferably 5 to 7. The solid complex, having a polymer containing both free acid and neutralized (salt) forms thus produces the appropriate pH on dispersion to produce a stable emulsion. For example, some pH adjustment is required with the materials of examples V, VI, and VII.

EXAMPLE X 1 grams of the product of example V was placed in 50 grams of water to form a 1% AI concentration. The pH was 3 and a stable dispersion did not form. The pH was adjusted, by addition of sodium hydroxide, to be above 5. Above a pH of 5, a stable dispersion was produced.

Utilizing the inventive polymer complexes, pesticide and herbicide formulations normally applied from organic solvents may be stored and handled as solids which are dispersable into stable aqueous emulsions prior to application. This substantially simplifies storage and handling of such materials, and reduces the potential for organic vapor emissions. In addition, the dispersions, being stable, allow uniform application from water without necessitating the incorporation of other stabilizing additives. This is particularly advantageous at the field point of use, where simply placing in water is all that is required before application.

While specific embodiments of the present invention have been shown and described, it will be understood by those skilled in the art that various changes or modifications could be made without varying from the scope of the present invention.

What is claimed is:

1. A solid complex of a polymer and a pesticide formulation, comprising a polymer having acid groups in a polymer matrix thereof and being capable of forming an insertion complex via hydrogen bonding with the pesticide formulation, the polymer selected from the group consisting of a maleic acid-methylvinylether alternating copolymer, a maleic acid-butylvinylether copolymer, polyacrylic acid, polymethacrylate, and pyrollidonylethyl-maleimide-methylvinylether-maleic acid copolymer, the pesticide being from the group consisting of metolachlor, acetochlor, pretilachlor, dimethachlor, alachlor and butachlor, the solid complex comprising from 10 to 90 percent by-weight pesticide formulation co-precipitated with the polymer.

2. The complex of claim 1 wherein the ratio of pesticide formulation to polymer is from 30–90% pesticide.

3. The complex of claim 1 wherein the ratio of pesticide formulation to polymer is from 40–60% pesticide.

* * * * *